US00PP28240P3

(12) United States Plant Patent
Kleinwee

(10) Patent No.: US PP28,240 P3
(45) Date of Patent: Aug. 1, 2017

(54) *PETUNIA* PLANT NAMED 'PEHY0017'

(50) Latin Name: *Petunia hybrida*
Varietal Denomination: PEHY0017

(71) Applicant: SYNGENTA PARTICIPATIONS AG, Basel (CH)

(72) Inventor: Theodorus Cornelis Maria van Kleinwee, Enkhuizen (NL)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 14/999,982

(22) Filed: Jul. 21, 2016

(65) Prior Publication Data

US 2017/0064895 P1 Mar. 2, 2017

(51) Int. Cl.
*A01H 5/02* (2006.01)

(52) U.S. Cl.
USPC ..... Plt./356.2

(58) Field of Classification Search
USPC ..... Plt./356.2, 356.16
CPC ..... A01H 5/02
See application file for complete search history.

*Primary Examiner* — Kent L Bell
(74) *Attorney, Agent, or Firm* — Dale Skalla

(57) ABSTRACT

A new *Petunia* plant named 'PEHY0017' particularly distinguished by its mounding plant habit, medium sized, blue colored flowers with a pattern of dark blue veining, medium green foliage, good branching and early flowering.

1 Drawing Sheet

Latin name of the genus and species of the plant claimed: *Petunia hybrida.*

Varietal denomination: 'PEHY0017'.

BACKGROUND OF THE NEW PLANT

The present invention comprises a new *Petunia*, botanically known as *Petunia hybrida*, and hereinafter referred to by the variety name 'PEHY0017'.

'PEHY0017' is a product of a planned breeding program. The new cultivar has a mounding plant habit, medium sized, blue colored flowers with a pattern of dark blue veining, medium green foliage, good branching and early flowering.

'PEHY0017' originated from a hybridization made in October 2010 in a controlled breeding environment in Enkhuizen, The Netherlands. The female parent was the unpatented proprietary plant designated 'P0192' with variable flower color, from light blue to blue depending on age, poor branching, and a very early flowering response.

The male parent of 'PEHY0017' was an unpatented proprietary plant identified as 'N0539-2' with a more semi-trailing habit, more vigour, late flowering and deep blue flower color.

The resulting seeds were sown in January 2011. 'PEHY0017' was selected as one flowering plant within the progeny of the stated cross in May 2011 in a controlled environment in Enkhuizen, The Netherlands The first act of asexual reproduction of 'PEHY0017' was accomplished when vegetative cuttings were propagated from the initial selection in June 2016 in a controlled environment in Enkhuizen, The Netherlands.

BRIEF SUMMARY OF INVENTION

Horticultural examination of plants grown from cuttings of the plant initiated in June 2011, and continuing thereafter, has demonstrated that the combination of characteristics as herein disclosed for 'PEHY0017' are firmly fixed and are retained through successive generations of asexual reproduction.

'PEHY0017' has not been observed under all possible environmental conditions. The phenotype may vary significantly with variations in environment such as temperature, light intensity, and day length.

A Plant Breeder's Right for this cultivar was applied for in the European Union on Sep. 2, 2015 and assigned No. 2015/2039. 'PEHY0017' has not been made publicly available prior to the effective filing date of this application, notwithstanding any disclosure that may have been made less than one year prior to the effective filing date of this application by the inventor or another who obtained 'PEHY0017' directly from the inventor.

The following traits have been repeatedly observed and are determined to be basic characteristics of the new variety. The combination of these characteristics distinguishes this *Petunia* as a new and distinct variety.

BRIEF DESCRIPTION OF THE PHOTOGRAPHS

The accompanying photographic drawings show typical flower and foliage characteristics of 'PEHY0017' with colors being as true as possible with an illustration of this type.

Figure 1:
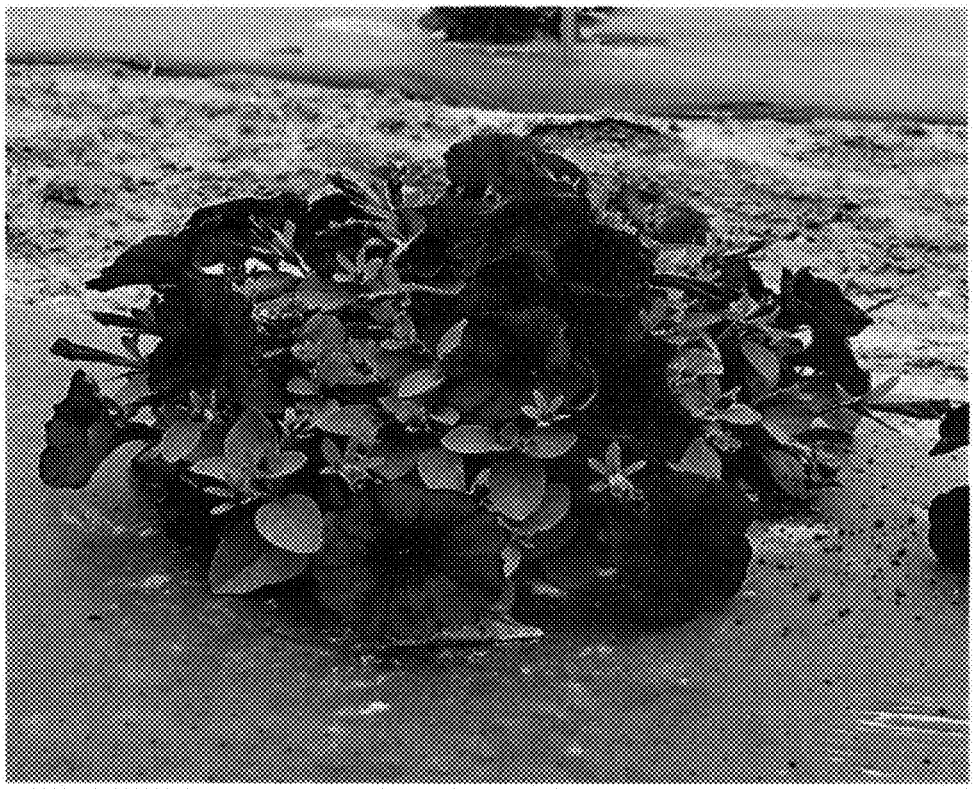
Figure 2:
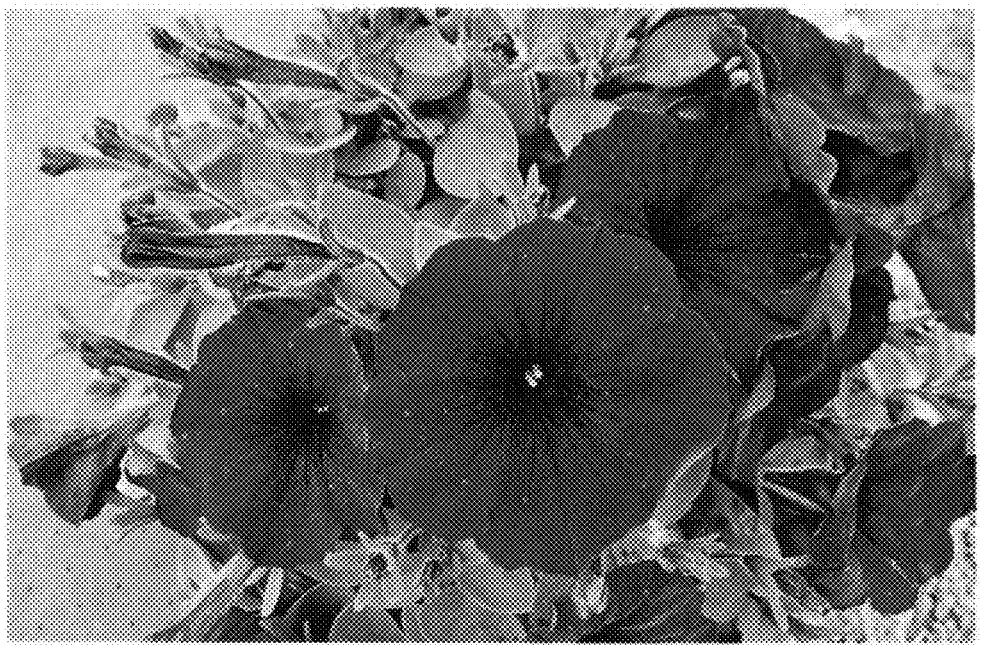

The photographic drawings show in FIG. 1. a flowering plant of the new variety and in FIG. 2. a close-up of the flowers.

DETAILED BOTANICAL DESCRIPTION

The aforementioned photographs were taken in July 2015 from plants growing in a field trial in Enkhuizen, The Netherlands. These plants were approximately 17 weeks of age.

The plant descriptions and measurements were taken in June 2016 in Andijk, The Netherlands on 16 week old plants that were growing in big containers outdoors.

Color references are made to The Royal Horticultural Society Colour Chart (R.H.S.) 2001.

TABLE 1

DIFFERENCES BETWEEN THE NEW VARIETY 'PEHY0017' AND A SIMILAR VARIETY

| | 'PEHY0017' | 'Keipabukas' (U.S. Plant Pat. No. 14748) |
|---|---|---|
| Flower color: | Deep purple, RHS 83A, but much deeper. | Deep RHS N87A to RHS 91D when flowers get old |
| Color of throat: | Very dark purple, almost black | Tube is white with some veins |
| Flowering response: | Early | Rather late |
| Leaf shape: | Ovate | Narrow elliptic |

Plant:

*Form, growth and habit.*—Mounding plant habit and development.

*Plant height.*—13 cm.

*Plant height (inflorescence included).*—15 cm.

*Plant diameter (width).*—25 cm.

Roots:

*Number of days to initiate and produce roots.*—16-22 days at about 22 degrees C.

*Type.*—Fine, fibrous, free branching.

*Color.*—RHS N155D.

Foliage:

*Arrangement.*—Alternate, simple.

*Immature leaf, color upper surface.*—RHS 137C.

*Immature leaf, color lower surface.*—RHS 144A.

*Mature leaf, color upper surface.*—RHS 137A.

*Mature leaf, color lower surface.*—RHS 138A.

*Length.*—4.5-5.0 cm.

*Width.*—2.8-3.5 cm.

*Shape.*—Ovate.

*Base shape.*—Attenuate to shortly attenuate.

*Apex shape.*—Acute.

*Margin.*—Entire.

*Texture, upper surface.*—Densely covered with short glandular hair.

*Lower surface.*—Densely covered with short glandular hair.

*Color of veins, upper surface.*—RHS 144A.

*Color of veins, lower surface.*—RHS 144A.

*Petiole color.*—RHS 144A.

*Length.*—0.2-0.4 cm.

*Diameter.*—0.3 cm.

*Petiole texture.*—Short glandular hair.

Stem:

*Quantity of main branches per plant.*—12.

*Color of stem.*—RHS 144A, occasionally anthocyanin coloration RHS 177A.

*Length of stem.*—12-15 cm.

*Diameter.*—0.6 cm at base.

*Length of internodes.*—2.0-5.5 cm.

*Texture.*—Dense, mostly glandular hairs of variable length.

*Color of pedicel.*—RHS 143C, with variable anthocyanin coloration, RHS 177A, most dominant just below the bud or inflorescence.

*Length of pedicel.*—2.2-4.2 cm.

*Diameter of pedicel.*—0.15-0.25 cm.

*Texture of pedicel.*—Densely covered with short glandular hairs.

Inflorescence:

*Type.*—Flowers solitary in upper leaf axis; flowers face mainly horizontally.

*Floret type.*—Funnel-shaped; 5 lobed petals; fused at the base.

*Blooming habit.*—Continuous flowering throughout the summer months, little affected by heat.

*Quantity of inflorescences per plant.*—Approximately 10.

*Lastingness of individual blooms on the plant.*—About 7 days.

*Fragrance.*—None.

Bud (just when opening):

*Color.*—Darker than RHS 83A.

*Length.*—4.2-5.0 cm.

*Width.*—0.7-0.9 cm.

*Shape.*—Cleft.

Immature inflorescence:

*Flower horizontal diameter.*—5.0-6.0 cm.

*Color petals, upper surface.*—Darker than RHS 83A, with veining that is even darker.

*Color petals, lower surface.*—RHS 83A.

Mature flower:

*Flower horizontal diameter.*—6.0-6.6 cm.

*Flower height (vertical).*—4.0 cm.

*Color upper surface.*—Darker than RHS 83A, with strong veining that is even darker.

*Color lower surface.*—RHS 83B.

*All petals.*—

*Apex shape.*—Truncate.

*Margin.*—Entire.

*Waviness of margin.*—Medium.

*Petal lobation.*—Weak to medium.

*Petal texture, upper surface.*—Papillose, glabrous.

*Petal texture, lower surface.*—Papillose; a few very short glandular.

*Corolla tube color outside.*—Darker than RHS 83A.

*Corolla tube color inside.*—Almost black, RHS N202A.

*Corolla tube length.*—3.0 cm.

*Corolla tube texture, outside.*—Pilose, glandular hairs.

*Corolla tube texture, inside.*—Glabrous.

Calyx:

*Color of sepal, upper surface.*—RHS 137B.

*Color of sepal, lower surface.*—RHS 137C.

*Length.*—2.0-2.2 cm.

*Width.*—0.6-0.7 cm.

*Shape.*—Ensiform.

*Apex shape.*—Acute.

*Base.*—Fused.

*Margins.*—Entire.

*Texture, upper surface.*—Densely covered with glandular hairs with variable length.

*Lower surface.*—Covered with short glandular hairs.

Reproductive organs:

*Pistil.*—1.

*Length.*—2.3-2.6 cm.

*Style color.*—RHS 83D at base, to almost black RHS 202A just below stigma.

*Style length.*—2.0-2.2 cm.

*Stigma color.*—N202A.

*Stamens.*—

*Quantity per flower.*—5.
*Color of filaments.*—RHS 144D at base to RHS 83D near anther.
*Length filaments.*—1.4-1.7 cm.
*Anther color.*—RHS 202C to RHS 84D.
*Anther length.*—0.05 cm.
*Anther shape.*—Rounded.
*Color of pollen.*—RHS 202C.
*Pollen amount.*—Moderate.
*Fertility/seed set.*—Has not been observed on this hybrid.
*Disease/pest resistance.*—Has not been observed on this hybrid.

What is claimed is:

1. A new and distinct variety of *Petunia* plant named 'PEHY0017' substantially as illustrated and described herein.

* * * * *